(12) United States Patent
Chen et al.

(10) Patent No.: US 10,472,563 B2
(45) Date of Patent: Nov. 12, 2019

(54) METHODS FOR MAKING IMPROVED QUANTUM DOT RESIN FORMULATIONS

(71) Applicants: Rohm and Haas Electronic Materials LLC, Marlborough, MA (US); Dow Global Technologies LLC, Midland, MI (US)

(72) Inventors: Liang Chen, Midland, MI (US); Leslie E. O'Leary, Midland, MI (US); Zhifeng Bai, Midland, MI (US); Yuming Lai, Midland, MI (US); Jake Joo, Somerville, MA (US)

(73) Assignees: Rohm and Haas Electronic Materials LLC, Marlborough, MA (US); Dow Global Technologies LLC, Midland, MI (US)

( * ) Notice: Subject to any disclaimer, the term of this patent is extended or adjusted under 35 U.S.C. 154(b) by 143 days.

(21) Appl. No.: 15/880,879

(22) Filed: Jan. 26, 2018

(65) Prior Publication Data

US 2018/0230377 A1    Aug. 16, 2018

Related U.S. Application Data

(60) Provisional application No. 62/459,923, filed on Feb. 16, 2017.

(51) Int. Cl.

| | |
|---|---|
| C07C 27/26 | (2006.01) |
| C07C 67/48 | (2006.01) |
| C09K 11/02 | (2006.01) |
| C09K 11/54 | (2006.01) |
| C09K 11/62 | (2006.01) |
| C09K 11/70 | (2006.01) |
| B01D 15/08 | (2006.01) |
| C08F 220/16 | (2006.01) |
| C09D 5/22 | (2006.01) |
| C09D 5/24 | (2006.01) |
| C09D 133/06 | (2006.01) |
| C09K 11/88 | (2006.01) |
| C08F 220/18 | (2006.01) |
| B82Y 20/00 | (2011.01) |
| B82Y 40/00 | (2011.01) |
| C08K 3/30 | (2006.01) |
| C08K 3/32 | (2006.01) |
| C08K 9/02 | (2006.01) |
| B82Y 30/00 | (2011.01) |

(52) U.S. Cl.
CPC ............ *C09K 11/025* (2013.01); *B01D 15/08* (2013.01); *C08F 220/16* (2013.01); *C08F 220/18* (2013.01); *C09D 5/22* (2013.01); *C09D 5/24* (2013.01); *C09D 133/062* (2013.01); *C09K 11/703* (2013.01); *C09K 11/883* (2013.01); *B82Y 20/00* (2013.01); *B82Y 30/00* (2013.01); *B82Y 40/00* (2013.01); *C07C 27/26* (2013.01); *C07C 67/48* (2013.01); *C08F 2800/20* (2013.01); *C08K 3/30* (2013.01); *C08K 3/32* (2013.01); *C08K 9/02* (2013.01); *C08K 2003/3036* (2013.01); *C09K 11/02* (2013.01); *C09K 11/54* (2013.01); *C09K 11/62* (2013.01); *C09K 11/70* (2013.01); *Y10S 438/962* (2013.01); *Y10S 977/774* (2013.01); *Y10S 977/818* (2013.01); *Y10S 977/824* (2013.01); *Y10S 977/892* (2013.01); *Y10S 977/95* (2013.01)

(58) Field of Classification Search
None
See application file for complete search history.

(56) References Cited

U.S. PATENT DOCUMENTS

| | | | |
|---|---|---|---|
| 6,322,901 B1 | 11/2001 | Bawendi et al. | |
| 7,557,028 B1 | 7/2009 | Scher et al. | |
| 7,588,828 B2 | 9/2009 | Mushtaq et al. | |
| 8,062,967 B1 | 11/2011 | Scher et al. | |

(Continued)

FOREIGN PATENT DOCUMENTS

JP    2005333777 A    12/2005

OTHER PUBLICATIONS

Armarego, W. L. F. and Chai, C. L. L. "Common Physical Techniques Used in Purification". Chap. 1 in Purification of Laboratory Chemicals. 7th ed. Elsevier, 2013. (Year: 2013).*

(Continued)

*Primary Examiner* — Richard A Huhn
(74) *Attorney, Agent, or Firm* — S. Matthew Cairns

(57) ABSTRACT

The present invention provides methods for making polymerizable monomer compositions comprising purifying a (b) monomer mixture of (i) one or more monomers having at least two polymerizable vinyl groups and (ii) one or more monomers having a single polymerizable vinyl group as part of a (meth)acrylate ester group by any one or more of treating the monomer mixture in an activated porous alumina or silica column, sieve drying the monomer mixture in a vacuum followed by drying over dried molecular sieves having average pore sizes of from 2 to 20 Angstroms, freeze-pump-thaw (FPT) treating by freezing the monomer mixture in a vessel or container to a temperature below $-75°$ C., degassing the monomer mixture by application of vacuum in the range of $10^2$ to $10^{-2}$ Pa, sealing the vessel or container under vacuum, and thawing the composition to room temperature; and, combining in an inert gas atmosphere the resulting monomer mixture (b) with a composition (a) of quantum dots in dry form or organic solvent solution.

10 Claims, No Drawings

(56) References Cited

U.S. PATENT DOCUMENTS

| | | |
|---|---|---|
| 8,847,197 B2 | 9/2014 | Pickett et al. |
| 8,884,273 B1 | 11/2014 | Scher et al. |
| 9,136,428 B2 | 9/2015 | Clough et al. |
| 9,206,350 B2 | 12/2015 | Choi et al. |
| 9,212,056 B2 | 12/2015 | Breen et al. |
| 9,469,538 B1 | 10/2016 | Scher et al. |
| 10,119,073 B2 | 11/2018 | Venkataraman et al. |
| 2009/0146202 A1 | 6/2009 | Leong et al. |
| 2010/0084629 A1 | 4/2010 | Park et al. |
| 2012/0113672 A1 | 5/2012 | Dubrow et al. |
| 2015/0047765 A1 | 2/2015 | Vo et al. |
| 2015/0166342 A1 | 6/2015 | Liu et al. |
| 2015/0236195 A1 | 8/2015 | Guo et al. |
| 2017/0218264 A1 | 8/2017 | Klimov et al. |

OTHER PUBLICATIONS

Co-Pending U.S. Appl. No. 15/062,608, filed Mar. 7, 2016.
Search report for corresponding Great Britain Application No. GB1802439.8 dated Nov. 8, 2018.
Gou, et al; Measurement of the Dissolved Oxygen Concentration in Acrylate Monomers With a Novel Photochemical Method; Journal of Polymer Science, Part A: Polymer Chemistry; vol. 42; Issue 5; pp. 1285-1292; Mar. 1, 2004.

* cited by examiner

METHODS FOR MAKING IMPROVED QUANTUM DOT RESIN FORMULATIONS

The present invention relates to methods for making polymerizable monomer compositions containing quantum dots, preferably, cadmium-free quantum dots, that provide improved initial quantum yield performance as well as to the compositions and polymer composites made with the compositions.

Semiconductor quantum dots (QD) provide optical absorption and emission (photoluminescence PL or electroluminescence EL) behaviors that enable their use in many display and lighting applications. Many QD have inorganic shells made of a larger bandgap material to confine electron and hole pairs within the core region and prevent any surface charge states. The outer shells or the QD themselves are then capped by organic ligands to reduce trap states of the shell that can lead to reduced quantum yield (QY). Typical organic ligands surrounding QD help QD to disperse in organic/aqueous solvents and have relatively long alkyl chains which provide high solubility in non-polar solvents or monomers. Unfortunately, QD are very susceptible to photooxidation during the light absorption and/or light conversion process. Also, moisture can have a similar impact. QD typically are encapsulated in a polymer matrix to protect them from adverse effects of water and oxygen. However, there remains a clear loss in QY when QD are transferred from a solvent solution to a monomer formulation and subsequent polymerization to form a QD polymer composite, such as a film.

U.S. patent application no. US 2009/0146202 A1 to Leong discloses organic memory devices comprising a control layer, an active layer and, between the two, a charge storing layer of nanoparticles on or within an organic dielectric copolymer material, wherein the polymer has been processed by solvent extraction to remove ionic impurities and form a polymer solution. The nanoparticles can be coated on the dielectric copolymer or can be part of the copolymer layer. Where the polymer solution and the nanoparticles are used together, the nanoparticles or QD are formed in situ in solution. Even if one were to extract ionic impurities from the polymer solution containing nanoparticles, Leong discloses only removal of salts or aqueous ions thereby resulting in an organic solvent solution of polymer. Such a method would not improve the performance of a formulation containing QD and polymerizable monomers.

The present inventors have endeavored to provide methods of making polymerizable monomer compositions containing QD and films thereof having improved initial quantum yield performance.

SUMMARY OF THE INVENTION

The present invention provides a polymerizable monomer composition comprising: (a) quantum dots; and (b) a monomer mixture of (i) one or more monomers having at least two polymerizable vinyl groups as part of a (meth)acrylate ester group or attached directly to an aromatic ring or a cycloaliphatic group and (ii) one or more monomers having a single polymerizable vinyl group as part of a (meth)acrylate ester group in which the ester contains a cycloaliphatic group or a $C_6$ to $C_{24}$ alkyl group, such as a fatty alkyl group, wherein the composition comprises 150 ppm or less, or, preferably, 60 ppm or less of $H_2O$ as determined by Karl Fisher Titration, for example, from 5 to 60 ppm, comprises 75 ppm or less or, preferably, 60 ppm or less of total dissolved oxygen as determined by a photochemical method as described in the reference (J. Polym. Sci. A: Polym. Chem. 2004, volume (42), pages 1285-1292), comprises 50 ppm or less, or, preferably, 25 ppm or less, for example, from 1 to 25 ppm, of total polymerization inhibitor compounds, such as hydroquinone and 150 ppm or less or, preferably, 100 ppm or less, for example, from 10 to 100 ppm of organic radically active molecules, such as radical initiators and photoinitiators.

In accordance with the polymerizable monomer composition of the present invention, the (a) quantum dots are preferably cadmium-free quantum dots such as, for example, ZnS, ZnSe, ZnTe, HgS, HgSe, HgTe, GaN, GaP, GaAs, InP, InAs or a mixture thereof, or, more preferably, the (a) quantum dots are core shell cadmium-free quantum dots that have a core shell structure wherein the shell material has a wider band gap than and a small lattice mismatch to the core material, such as, for example, those having a III-V nanoparticle core, and a II-VI nanoparticle shell or, even more preferably, the (a) quantum dots are cadmium-free quantum dots having an indium containing, InP, GaP, GaN, GaAs or InAs core with a zinc containing, ZnS, ZnSe, ZnTe, HgS, HgSe, or HgTe shell.

In accordance with the polymerizable monomer composition of the present invention, the monomer mixture (b) comprises (i) divinyl benzene, tricyclodecane dimethanol diacrylate, isobornyl dimethacrylate, or mixtures thereof and (b)(ii) one or more monomers having a single polymerizable vinyl group as part of a (meth)acrylate ester group in which the ester contains a cycloaliphatic group or a $C_6$ to $C_{24}$ alkyl group.

In accordance with the polymerizable monomer composition of the present invention, the monomer mixture (b) comprises (i) one or more monomers having at least two polymerizable vinyl groups as part of a (meth)acrylate ester group or attached directly to an aromatic ring or a cycloaliphatic group and (b)(ii) isobornyl acrylate (IBOA).

In accordance with the polymerizable monomer composition of the present invention, the composition comprises (a) from 0.001 to 5 wt. % or, preferably, from 0.01 to 5 wt. % or, more preferably, from 0.1 to 5 wt. % of quantum dots, (b) from 0.5 to 40 wt. % or, preferably, from 0.5 to 10 wt. % of the (b) (i) one or more monomers having at least two polymerizable vinyl groups as part of a (meth)acrylate ester group or attached directly to an aromatic ring or a cycloaliphatic group, and from 55 to 95 wt. % or from 55 to 94.999 wt. % or from 55 to 94.99 wt. % or from 55 to 94.9 wt. %, or, preferably, from 65 to 92 wt. % of the (b) (ii) one or more monomers having a single polymerizable vinyl group as part of a (meth)acrylate ester group in which the ester contains a cycloaliphatic group or a $C_6$ to $C_{24}$ alkyl group, all wt. % s based on the total solids content of the composition.

In a second aspect, the present invention provides methods for making polymerizable monomer compositions comprising:

Purifying a (b) monomer mixture of (i) one or more monomers having at least two polymerizable vinyl groups as part of a (meth)acrylate ester group or attached directly to an aromatic ring or a cycloaliphatic group and (ii) one or more monomers having a single polymerizable vinyl group as part of a (meth)acrylate ester group in which the ester contains a cycloaliphatic group or a $C_6$ to $C_{24}$ alkyl group, such as a fatty alkyl group, by any one or more of: Treating the monomer mixture in an activated porous alumina or silica column having, for example, a surface area of from 100 to 300 m$^2$/g, such as 130 to 180 m$^2$/g, for example, 155 m$^2$/g; sieve drying the monomer mixture in a vacuum followed by drying over dried molecular sieves, such as zeolites, having weight average pore sizes of from 2 to 20 Angstroms, or, preferably, from 2.5 to 10 Angstroms; freeze-pump-thaw (FPT) treating by freezing the monomer mixture in a vessel or container to a temperature of −75° C. or less, followed by degassing the monomer mixture by application of vacuum, for example, $10^2$ to $1×10^{−2}$ Pa, and sealing the vessel or container under vacuum and thawing the composition to room temperature, preferably, repeating FPT until no bubbles are visible on thawing;

storing the purified monomer mixture (b) in a dry and inert gas, such as nitrogen; and, combining in an inert atmosphere, such as under nitrogen, the resulting monomer mixture (b) with a composition (a) of quantum dots in dry form or organic solvent solution, preferably, in dry form or followed by drying, to make a polymerizable monomer composition that comprises 150 ppm or less, or, preferably, 60 ppm or less of $H_2O$, for example, from 5 to 60 ppm, comprises 75 ppm or less, or, preferably, 60 ppm or less of total dissolved oxygen as determined by a photochemical method as described in the reference (J. Polym. Sci. A: Polym. Chem. 2004, volume 42, pages 1285-1292), comprises 50 ppm or less, or, preferably, 25 ppm or less, for example, from 1 to 25 ppm, of total polymerization inhibitor compounds, such as, for example, quinones, such as monomethyl ether hydroquinone (MEHQ), hydroquinone and N-oxyl compounds, such as 4-hydroxy-2,2,6,6-tetramethylpiperidinooxyl (4-HT), and 150 ppm or less or, preferably, 100 ppm or less, for example, from 10 to 100 ppm of organic radically active molecules, such as radical initiators and photoinitiators.

In accordance with the methods of the present invention in which the purifying of the monomer mixture (b) preferably comprises freeze-pump-thaw (FPT) treating, followed by drying the resulting treated monomer mixture over a dried molecular sieve.

In accordance with the methods of the present invention in which the purifying of the monomer mixture (b) comprises degassing the monomer mixture under a vacuum of from $10^2$ to $10^{−2}$ Pa for 1 hour and then treating it in an activated porous alumina or silica column, wherein the activated alumina or silica has been dried by thermally treating at from 60 to 120° C. in a vacuum of from $10^2$ to $1×10^{−2}$ Pa for from 2 to 16 hours, and then packed into a column, such as a disposable polypropylene column.

In accordance with the methods of the present invention in which the purifying of the monomer mixture (b) comprises degassing the monomer mixture under a vacuum of from $10^2$ to $10^{−2}$ Pa and then drying it by exposure to or, preferably, by mixing with molecular sieves which have been dehydrated at a temperature of from 75 to 200° C., for example, 120 to 200° C. for a period of 4 to 24 hours and kept in an inert atmosphere, such as nitrogen gas.

In accordance with the methods of the present invention in which in the combining of the monomer mixture (b) and the composition (a) of quantum dots, the (a) quantum dots are dried under vacuum to remove any organic solvent before the combining or the polymerizable monomer composition together with the (a) quantum dots is dried under vacuum to remove any organic solvent.

In accordance with the methods of the present invention in which in the combining of the monomer mixture (b) and the composition (a) of quantum dots, the quantum dots preferably comprise cadmium-free quantum dots such as, for example, ZnS, ZnSe, ZnTe, HgS, HgSe, HgTe, GaN, GaP, GaAs, InP, InAs or a mixture thereof, or, more preferably, the composition (a) of quantum dots comprises core shell cadmium-free quantum dots that have a core shell structure wherein the shell material has a wider band gap than and a small lattice mismatch to the core material, such as, for example, those having a III-V nanoparticle core, and a II-VI nanoparticle shell or, even more preferably, the quantum dots comprise cadmium-free quantum dots having an indium containing core, or, even more preferably, the (a) quantum dots are cadmium-free quantum dots having an InP, GaP, GaN, GaAs or InAs core with zinc containing, a ZnS, ZnSe, ZnTe, HgS, HgSe, or an HgTe shell.

In accordance with the methods of the present invention, the monomer mixture (b) comprises (i) divinyl benzene, tricyclodecane dimethanol diacrylate, isobornyl dimethacrylate, or mixtures thereof and (b)(ii) one or more monomers having a single polymerizable vinyl group as part of a (meth)acrylate ester group in which the ester contains a cycloaliphatic group or a $C_6$ to $C_{24}$ alkyl group.

In accordance with the methods of the present invention, the monomer mixture (b) comprises (i) one or more monomers having at least two polymerizable vinyl groups as part of a (meth)acrylate ester group or attached directly to an aromatic ring or a cycloaliphatic group and (b)(ii) isobornyl acrylate (IBOA).

In accordance with the methods of the present invention, the monomer mixture (b) comprises, as solids, from 0.5 to 40 weight parts or, preferably, from 0.5 to 10 weight parts of the (b) (i) one or more monomers having at least two polymerizable vinyl groups as part of a (meth)acrylate ester group or attached directly to an aromatic ring or a cycloaliphatic group, and from 55 to 95 weight parts or, preferably, from 65 to 92 weight parts of the (b) (ii) one or more monomers having a single polymerizable vinyl group as part of a (meth)acrylate ester group in which the ester contains a cycloaliphatic group or a $C_6$ to $C_{24}$ alkyl group.

In accordance with the methods of the present invention in which the method further comprises polymerizing the polymerizable monomer composition to form a polymer composite, such as a film.

In a third aspect, the present invention provides polymer composites that comprise a polymer formed from the polymerizable monomer composition of the (a) quantum dots and the (b) (i) one or more monomers having at least two polymerizable vinyl groups as part of a (meth)acrylate ester group or attached directly to an aromatic ring or a cycloaliphatic group, preferably, tricyclodecane dimethanol diacrylate, isobornyl dimethacrylate, divinyl benzene, or mixtures thereof and the (ii) one or more monomers having a single polymerizable vinyl group as part of a (meth)acrylate ester group in which the ester contains a cycloaliphatic group or a $C_6$ to $C_{24}$ alkyl group.

In accordance with the polymer composite of the present invention, wherein the (a) quantum dots are cadmium-free quantum dots or, preferably, core-shell quantum dots.

In accordance with the polymer composite of the present invention in which the composite is a film.

In accordance with the polymer composite of the present invention in which the polymer composite comprises part of a multilayer film, laminate or assembly which also comprises an outer layer on each side of the polymer composite film. Preferably, the outer layer is an oxygen barrier, such as, for example, polyethylene terephthalate (PET) which also inhibits passage of moisture.

Unless otherwise specified, percentages are weight percentages (wt. %) and temperatures are in ° C.

Unless otherwise specified, operations and examples were performed at room temperature (20-25° C.).

Unless otherwise specified, boiling points are measured at atmospheric pressure (ca. 101 kPa).

Unless otherwise indicated, any term containing parentheses refers, alternatively, to the whole term as if no parentheses were present and the term without them, and combinations of each alternative. Thus, the term "(meth)acrylate" means acrylate, methacrylate or mixtures thereof.

All ranges are inclusive and combinable. For example, the term "a range of 50 to 3000 cPs, or 100 or more cPs" would include each of 50 to 100 cPs, 50 to 3000 cPs and 100 to 3000 cPs.

As used herein, the term "ASTM" refers to publications of ASTM International, West Conshohocken, Pa.

As used herein, the term "average pore size" refers to the pore size of an indicated material as provided by manufacturer documentation determined by the BET surface area method.

As used herein, the term "band gap" refers to the energy gap between the highest occupied molecular orbital (HOMO) and the lowest unoccupied molecular orbital (LUMO) in a given quantum dot or layer thereof, as measured by ultraviolet photoelectron spectroscopy (UPS).

As used herein, the term "solids" refers to any material that does not volatilize in the methods of the present invention and, thereby, that ends up in a polymer composite of the present invention. Ammonia, water and volatile organic solvents (VOCs) are not considered solids. In accordance with the present invention, the photoluminescent quantum yield (PLQY) of polymer composites was improved when quantum dot (QD) containing compositions were dispersed in monomer mixtures of acrylic or vinyl monomers which have been purified. In the present invention, most impurities such as water, oxygen, radical initiators, photoinitiators and polymerization inhibitors were removed from the polymerizable monomer compositions used to make the polymer composites. The present inventors have found that the presence of these impurities during QD transfer to a monomer mixture and subsequent polymerization of QD containing monomer mixture formulations will negatively impact PLQY. Other impurities, such as some dissolved ionic species, acids, alcohols, ketones, and aldehydes, can absorb light or are also deleterious to the PLQY of QDs during QD synthesis and in the long-term operation of QDs. By removing impurities during formulation, higher initial or time zero performance in polymer composites or films containing the QD was achieved.

Quantum dots are well known in the art, see, e.g., U.S patent publication no. US2012/0113672 A, to Dubrow et al. Preferably, the quantum dots in the polymer composite of the present invention are cadmium free quantum dots, or, more preferably, cadmium free core-shell quantum dots.

Suitable quantum dots and core-shell quantum dots may include any of those disclosed in any of U.S. Pat. No. 7,588,828 B2, to Mushtaq et al., for example, the quantum dots containing indium enriched InP cores, such as those formed by contacting InP with an indium carboxylate (i.e., an indium (Ill) carboxylate), such as indium laurate; those disclosed in U.S. patent publication no. 2015/0236195 A1, to Guo et al; those disclosed in U.S. patent publication no. US2015/0166342 A1 to Mingjun et al.; the Group III-IV semiconductor nanostructures, such as in U.S. Pat. No. 7,557,028 B1 to Scher et al., U.S. Pat. No. 8,062,967 B1 to Scher et al., U.S. patent no. U.S. Pat. No. 8,884,273 B1 to Scher et al., or U.S. Pat. No. 9,469,538 B1 to Scher et al.; nanocrystals having cores with a Group IIIA and a Group VA element, such as in U.S. Pat. No. 9,136,428 B2 to Clough et al.; the nanoparticles disclosed in U.S. Pat. No. 9,212,056 B2 to Breen et al.; or the nanocrystalline materials disclosed in U.S. Pat. No. 6,322,901 B1 to Bawendi et al.

Acceptable efficiency (PLQY) for a cadmium free quantum dot material is above 40%, or, preferably, above 60%, or, more preferably, 75% or higher, such as from 75 to 95%.

Preferably, the polymerizable vinyl groups in the (b) monomer mixture are (meth)acrylate ester groups ($CH_2$=C(R)C(O)O—, where R is H or $CH_3$; also known as (meth)acryloyloxy.

Preferably, the monomers in the (b) monomer mixture have only carbon, hydrogen, oxygen and nitrogen atoms; or, more preferably, have only carbon, hydrogen and oxygen atoms.

In the (b)(i) one or more monomers having at least two polymerizable vinyl groups as part of a (meth)acrylate ester group or attached directly to an aromatic ring or a cycloaliphatic group, the aromatic ring can be e.g., a benzene, naphthalene or pyridine ring or, preferably, the aromatic ring has from three to twenty carbon atoms, or, preferably from five to fifteen carbon atoms. Preferably, the aromatic ring contains no heteroatoms and has from six to fifteen carbon atoms, preferably from six to twelve carbon atoms.

Preferably, (b) (i) one or more monomers having at least two polymerizable vinyl groups as part of a (meth)acrylate ester group or attached directly to an aromatic ring or a cycloaliphatic group has from two to six polymerizable vinyl groups, or, more preferably, no more than four polymerizable vinyl groups.

Especially preferred monomers (b)(i) having at least two polymerizable vinyl groups as part of a (meth)acrylate ester group include tricyclo[5.2.1.0$^{2,6}$]decane dimethanol diacrylate, bisphenol A dimethacrylate, 2-butyl-2-ethyl-1,3-propanediol dimethacrylate, 1,10-bis(acryloyloxy)decane and

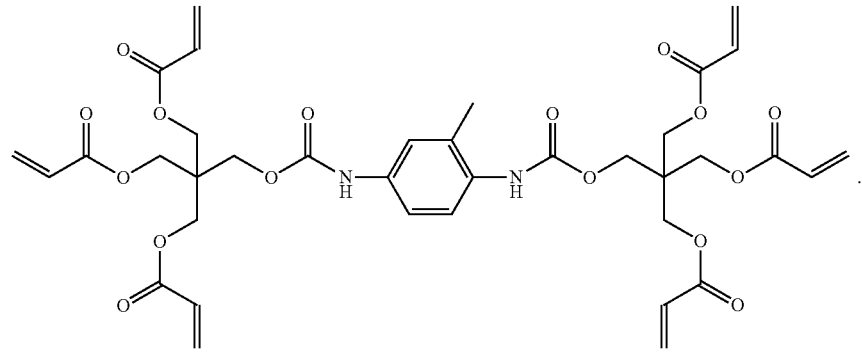

(A)

The polymer composite in accordance with the present invention further comprises polymerized units of (b)(ii) one or more monomers having a single polymerizable vinyl group as part of a (meth)acrylate ester group in which the ester contains a cycloaliphatic group or a $C_6$ to $C_{24}$ alkyl group. Preferably, such a monomer (b)(ii) is an aliphatic or cycloaliphatic monomer, such as isobornyl acrylate (IBOA).

Especially preferred (b)(ii) monomers having a single polymerizable vinyl group as part of a (meth)acrylate ester group in which the ester contains a cycloaliphatic group or a $C_6$ to $C_{24}$ alkyl group include isobornyl acrylate, 3,5,5-trimethylhexyl acrylate, dodecyl acrylate, decyl acrylate, tridecyl acrylate, isodecyl acrylate, L-menthyl acrylate, tricyclo[$5.2.1.0^{2,6}$]decylmethyl acrylate, 3,3,5-trimethylcyclohexyl methacrylate and 3,3,5-trimethylcyclohexyl methacrylate.

Preferably, the polymer composite of the present invention is part of a multilayer film, laminate or assembly which also comprises an outer layer on each side of the polymer composite. Preferably, the outer layer is an oxygen barrier which also inhibits passage of moisture. Preferably, the outer layer comprises a polymer composite, preferably one comprising polyethylene terephthalate (PET), polyaryletherketones, polyimides, polyolefins, polycarbonate, polymethyl methacrylate (PMMA), polystyrene, or a combination thereof. Preferably, the outer layer further comprises oxides or nitrides, preferably silicon oxides, titanium dioxide, aluminum oxide, silicon nitrides or a combination thereof. Preferably the oxides or nitrides are coated on the surface of the polymer composite facing the QD layer Preferably, each outer layer comprises a polymer composite having a thickness from 25 to 150 microns (preferably 50 to 100 microns) and an oxide/nitride layer having a thickness from 10 to 100 nm (preferably 30 to 70 nm).

In accordance with the polymer composites of the present invention, the outer layer of a multilayer film, laminate or assembly preferably comprises at least two polymer composite layers and/or at least two oxide/nitride layers. In any multilayer film of the present invention, different layers may be of differing composition. Preferably, the outer layers have a very low oxygen transmission rate (OTR, $<10^{-1}$ cc/m²/day) and low water vapor transmission rate (WVTR, $<10^{-2}$ g/m²/day).

Preferably, the polymer composite in the outer layers has a Tg from 60 to 200° C.; or, more preferably, at least 90° C., or, most preferably, at least 100° C.

Preferably, the thickness of a polymer composite in accordance with the present invention ranges from 20 to 500 microns, preferably at least 50 microns, preferably at least 70 microns, preferably at least 80 microns, preferably at least 90 microns; preferably no greater than 400 microns, preferably no greater than 300 microns, preferably no greater than 250 microns, preferably no greater than 200 microns, preferably no greater than 160 microns. Preferably, the thickness of each outer layer is from 20 to 100 microns, preferably from 25 to 75 microns.

Preferably, the polymer composite of this invention is prepared by free radical polymerization of the formulation prepared by mixing the (b) monomer mixture with a composition (a) of one or more QDs, and any optional additives. Preferably, the formulation is coated on a first outer layer prior to curing by typical methods, e.g., spin coating, slot die coating, gravure, ink jet and spray coating. Preferably, curing is initiated by exposing the formulation to ultraviolet light or heat, preferably ultraviolet light, preferably in the UVA range.

Preferably, the polymer composite of the present invention comprises as solids from 0.01 to 5 wt. % of quantum dots, preferably at least 0.025 wt. %, preferably at least 0.03 wt. %; preferably no more than 4 wt. %, preferably no more than 3 wt. %, preferably no more than 2 wt. %.

Preferably, the quantum dots comprise CdS, CdSe, CdTe, ZnS, ZnSe, ZnTe, HgS, HgSe, HgTe, GaN, GaP, GaAs, InP, InAs or a combination thereof. More preferably, the quantum dots are cadmium-free. Most preferably, the quantum dots are core-shell quantum dots, such as core-shell cadmium-free quantum dots.

Preferably, the compositions of (a) quantum dots comprise ligands surrounding the inorganic part of quantum dots that have non-polar components. Preferred ligands include, for example, include trioctyl phosphine oxide, dodecanethiol and fatty acid salts (e.g., stearate salts, oleic acid salts).

Other additives which may be incorporated into the polymerizable monomer compositions or polymer composites of the present invention include ultraviolet (UV) stabilizers, antioxidants, scattering agents to improve light extraction, and thickeners to increase viscosity (e.g., urethane acrylate oligomers). Preferably, any UV stabilizers in the polymerizable monomer compositions are used in amounts of only up to 100 ppm, or preferably, up to 50 ppm.

Preferred thickeners include urethane acrylates, cellulose ethers, cellulose acrylic esters, polystyrene polymers, polystyrene block copolymers, acrylic resin and polyolefin elastomers. Preferably, polystyrene, acrylic and polyolefin thickeners have a Mw ranging from 50,000 to 400,000; preferably from 100,000 to 200,000. Preferably, cellulose ethers have Mw ranging from 1,000 to 100,000.

Urethane acrylate oligomers can have polyester, polyether, polybutadiene, or polycaprolactone backbones between the acrylate groups they contain. They can have difunctional, trifuctional, hexafunctional reactivities. Viscosities of such oligomers can range from 1000 to 200,000 cPs at 50 C. For non-polar ligand QDs, polybutadiene urethane acrylate oligomers are preferred.

Preferred forms for the polymer composite include, e.g., composites, beads, strips, rods, cubes and plates. The polymer composite is useful in many applications, including, e.g., displays, lighting and medical applications. Preferred display applications include public information displays, signage, televisions, monitors, mobile phones, tablets, laptops, automotive and other dashboards, and watches.

EXAMPLES

The following examples illustrate the present invention. Unless otherwise indicated, all units of temperature are room temperature and all units of pressure are standard pressure or 101 kPa.

The following test methods were used:

Film thicknesses were determined by measurement of the cured films with a micrometer and then subtracting out the thickness of any barrier film thickness.

Photoluminescent Quantum Yield (PLQY)

In handling both liquid and films, photoluminescent Quantum Yield (PLQY), was measured with a Quantaurus-QY Absolute PL quantum yield spectrometer ($C_{11347}$-01 model) (Hamamatsu Photonics KK, Hamamatsu City, Japan). For each reported example, a total of three (3) measurements were taken from three (3) randomly selected points in each indicated analyte substrate and the indicated PLQY represents an average of the measurements taken.

Full-width half-max of the emission peak (FWHM) was measured with a Quantaurus-QY Absolute PL quantum yield spectrometer (C11347-01 model) integrating sphere (Hamamatsu Photonics KK).

Film thicknesses were determined by measurement of the cured films with a micrometer and then subtraction of the barrier film thickness.

Peak emission wavelength (PWL) was determined using Quantaurus-QY Absolute PL quantum yield spectrometer (C11347-01 model, Hamamatsu Photonics KK); for green QD in the examples, below, the target wavelength is from 520 to 540 nm; for red QD, the target wavelength is from 620 to 640 nm.

Karl-Fischer Titration:

Water content of monomers was analyzed by a Metrohm model 831 coulometric KARL FISCHER titrator (Metrohm Ltd, Herisau, Switzerland), calibrated as set forth in the manufacturer's literature and 703 Ti stand (Metrohm).

Monomer Purification Methods:

The following methods were used, as indicated, in the Examples that follow:

Freeze Pump Thaw (FPT):

The indicated monomer mixture was loaded into 20 mL scintillation vials. If sieves were used to dry the monomers, the sieves were added to the vial, and then the vial was fitted with a septum. The vials were submerged into liquid $N_2$ until the monomer had frozen (freeze). Once frozen, vacuum (1-0.1 Pa) was pulled to evacuate the headspace using a needle fitting on a Schlenk line (pump). The monomers were allowed to thaw under static vacuum until completely melted. Freeze-pump-thaw cycles were performed 3 times or until bubbles were no longer visible on the thaw cycles. Freeze-pump-thaw (FPT) purified monomer vials were backfilled with $N_2$, and then brought into an $N_2$ filled glovebox for subsequent handling. FPT monomers were used within 48 hours of purification.

Column Purification:

Activated Aluminum oxide (pH 4.5-9.5 in water, Aldrich, St. Louis, Mo.) was dried at 80° C. in vacuum for 4 h, and then packed into a disposable polypropylene column. The indicated monomer(s) was/were degassed in a vacuum oven (0.1-1 Pa) for 1 hour and then passed through the column slowly. Columns were run in inert atmosphere and purified monomers were stored in a nitrogen purge box. Purified monomers were used within 48 hours of purification.

Sieve Drying:

In the indicated Example, zeolite molecular sieves (4 Å average particle size) were used to dry monomers. Sieves were dehydrated in a 110° C. oven overnight and loaded into a $N_2$ filled glovebox while hot. Monomers were dried. Sieves were added to the monomers in the $N_2$ filled glovebox, were gently shaken, and then allowed to sit at room temperature for several hours prior to use. Sieve dried monomers were used within 48 hours of purification.

Abbreviations used in Examples:

IBOA is isobornyl acrylate; SR833 is tricyclo[5.2.1.0$^{2,6}$] decane dimethanol diacrylate; I-819 and I-651 are IRGACURE photoactive polymerization initiators (BASF AG, Leverkusen, DE); Finex™ zinc oxide particles (Sakai Chemical Industry co., LTD., Japan); and CFQD stands for cadmium free quantum dots. Green CFQD comprise core-shell QDs having Indium containing cores and exhibit an 73.9% QY, 44.1 nm FWHM, and a 534.4 nm PWL (at absorbance=0.3); Red CFQD comprise core-shell QDs that have indium containing cores and exhibit an 85% QY, 52.8 nm FWHM, and a 630 nm PWL (at absorbance=0.35).

Unless otherwise indicated, in the following Examples, the formulations were prepared, as follows:

All QD and monomer mixture formulations were prepared in an inert environment. After all indicated components except quantum dots or quantum dot solutions were loaded to a crimp vial, the vial was degassed and mixed for 3 to 5 minutes using a dual axis planetary mixer (THINKY ARE-310, Thinky CA). Quantum dots were transferred from toluene to monomer by removing the toluene from the QDs by nitrogen purge for 10 min, and then the dried QD powder was dispersed in the indicated monomer mixture. The quantum dots were pre-dispersed in isobornyl acrylate (IBOA) or the indicated monomer mixture, then mixed with the other components followed by mixing using a dual axis planetary mixer for 1 min in $N_2$ atmosphere. Monomer mixture components were combined with the dried QD powder after treating in the indicated fashion, which includes a short degas to introduce them to an inert atmosphere (Comparative only) or were purified by running over activated alumina column (column purified), drying with molecular sieves for >2 h (sieve dried), 3 cycles of freeze-pump thaw with or without sieves (FPT w/sieve or FPT only), or degassed at room temperature by application of vacuum for 48-72 h (RT degas).

Film Preparation:

Films of the formulations were prepared by lamination of the resin formulations between two i-Component PET barrier films. Approximately 2 mL of resin was dispensed on the bottom film and the top has applied with a gap coating bar with gap setup based on desired film thickness. Samples were cured in a Fusion UV F300S or a FUSION UV SYSTEMS, INC (DRS-10/12 QNH, Fusion UV Systems, Inc., Gaithersburg, Md.) curing system with UVA ~400 mJ/cm$^2$.

Impact of Monomer Purification on PLQY:

Solution PLQY was used to determine the compatibility between QDs and monomers using approximately 1 gram of each solution (0.025 wt. % QD solids, based on the total weight of the composition) in Table 1, below, to a 1 mL vial and measuring PLQY at 450 nm excitation.

TABLE 1

Solution PLQY measurement

| Example | QDs | Composition with QD[1] | Absorbance | QY (%) | Peak Wavelength | Peak FWHM |
|---|---|---|---|---|---|---|
| 1* | Green | in Toluene (anhydrous with molecular sieves) | 0.300 | 73.9 | 534.4 | 44.1 |
| 2* | Green | degassed IBOA | 0.315 | 59.7 | | |
| 3 | Green | Column purified degassed IBOA | 0.374 | 71.5 | | |
| 4* | Green | Column purified degassed IBOA + 400 ppm MEHQ | 0.272 | 68.8 | | |
| 5* | Green | Degassed IBOA:SR833 (3:2 by weight) | 0.356 | 55.8 | | |
| 6 | Green | Column purified degassed IBOA:SR833 (3:2 by weight) | 0.264 | 71.3 | | |
| 7 | Green | IBOA FPT w/sieve | 0.26 | 72.3 | | |
| 8 | Green | IBOA Molecular Sieve dried | 0.29 | 67.6 | | |

TABLE 1-continued

Solution PLQY measurement

| Example | QDs | Composition with QD[1] | Absorbance | QY (%) | Peak Wavelength | Peak FWHM |
|---|---|---|---|---|---|---|
| 9 | Green | IBOA FPT only | 0.26 | 67.9 | | |
| 10* | Red | in Toluene (anhydrous with molecular sieves) | 0.35 | 85.0 | 630 | 52.8 |
| 11* | Red | degassed IBOA | 0.34 | 74.0 | | |
| 12 | Red | Column purified degassed IBOA | 0.40 | 86.0 | | |
| 13* | Red | Column purified IBOA + 1500 ppm water | 0.28 | 79.0 | | |

*Denotes Comparative Example;
[1]Degassed materials treated 60 min under vacuum (0.1-1 Pa).

As shown in Table 1, above, quantum dots exhibit a decent quantum yield (QY) in solvent (see Comparative Examples 1 and 10) but lose much of that QY upon transfer to a monomer mixture or monomer formulation (see Comparative Examples 2 and 11). However, column purification, FPT or the combination of FPT with sieve drying retains much of the QY of the original QY of the quantum dot solution after transfer into a monomer mixture regardless of the monomers used. See Examples 3, 6, 7 and 12. Merely sieve drying retains nearly as much of the QY of the quantum dot solution as does FPT. See Examples 8 and 9.

TABLE 2

Characterization Of Water Content By Karl-Fischer Titration

| Example[1] | ppm Water |
|---|---|
| 1A* - Degassed IBOA | 252 ± 16 |
| 2A - IBOA (degassed and dried by molecular sieves) | ND (<50) |
| 3A - IBOA (degassed and purified by AlOx column) | ND (<50) |
| 4A* - IBOA (degassed by freeze-pump-thaw) | 303 |
| 5A - IBOA (degassed by freeze-pump-thaw with drying over molecular sieves) | ND (<50) |
| 6A* - IBOA (degassed and purified by AlOx column and then spiked with water) | 785 |

*Denotes Comparative Example;
[1]Degassed materials treated 60 min under vacuum (0.1-1 Pa).

As shown in Table 2, above, sieve drying and column purification effectively dries a monomer mixture; however, FPT alone, without separately drying does not dry the monomer mixture.

The formulations in Table 3, below, were drawn to make films of a consistent thickness using a bar coater (Paul N. Gardner Co., FL, USA) and PLQY was measured for each film. Each films was prepared by lamination of the indicated formulations between two i-Component PET barrier films. Approximately 2 mL of resin was dispensed on the bottom barrier film and was drawn down with a gap coating bar having a 250 to 300 (10 mil-12 mil) gap to insure the desired film thickness. All formulations were cured using a DRS-10/12 QNH at, 500 mJ/cm$^2$ UV curing intensity (Fusion UV Systems, Inc., Gaithersburg, Md.). Results are presented in Table 4, below.

TABLE 3

QD formulation (all parts by weight)

| | Film Formulation | | | |
|---|---|---|---|---|
| | 14[1] | 15* | 16[2] | 17* |
| IBOA | 60.036 | 60.036 | 58.31 | 58.31 |
| SR833 | 36.438 | 36.438 | 38.07 | 38.07 |
| I-819 | 0.901 | 0.901 | 1.00 | 1.00 |
| Finex 30S LP2 zinc oxide | 2.125 | 2.125 | 2.13 | 2.13 |
| Green QDs | 0.5 | 0.5 | | |
| Red QDs | | | 0.50 | 0.50 |
| Barrier film | i-component | i-component | i-component | i-component |
| Target resin optical density (OD)/g | 3.1 | 3.1 | 3.1 | 3.1 |

*Denotes Comparative Example;
[1]Purified monomers by AlOx column;
[2]Purified monomers by sieve drying.

TABLE 4

Characterization of Film PLQY

| Film | PLQY (%) | Absorbance | Peak (nm) | FWHM (nm) |
|---|---|---|---|---|
| 14 | 44.4 | 0.200 | 535.9 | 44.1 |
| 15* | 41.5 | 0.216 | 534.4 | 45.3 |
| 16 | 50.0 | 0.327 | 640.4 | 54.6 |
| 17* | 45.7 | 0.306 | 641.9 | 54.5 |

*Denotes Comparative Example.

As shown in Table 4, above, the purified compositions of the present invention show a significant improvement in initial quantum yield after column purification.

In the following Examples, formulations of monomer mixtures as indicated in Table 5, below, and QDs were handled, as indicated above with the degassed IBOA purified over an alumina column. Each QD composition was added into the monomer based on the formulation below in an inert atmosphere. 1.0 gram of each formulation was loaded into a glass vial and measured the PLQY using the Quantaurus quantum yield spectrometer. Loading of QD in monomer is 0.0025 wt. %, based on total weight of the formulation. Testing results are shown in Table 6, below.

TABLE 5

| Example | QD | QD toluene stock solution | IBOA | quantity |
|---|---|---|---|---|
| 18 | CdSe/ZnS core-shell (red) | 5 mg | Degassed and column purified | 1.0 g |
| 19* | CdSe/ZnS core-shell (red) | 5 mg | Degassed | 1.0 g |
| 20 | InP/ZnS core-shell (red) | 5 mg | Degassed and column purified | 1.0 g |
| 21* | InP/ZnS core-shell (red) | 5 mg | Degassed | 1.0 g |

*Denotes Comparative Example.

TABLE 6

Formulation Performance

| Example | PLQY | Absorption at 450 nm | Peak Red Wavelength | Peak FWHM |
|---|---|---|---|---|
| 18 | 0.473 | 0.212 | 615.81 | 28.79 |
| 19* | 0.448 | 0.18 | 616.56 | 29.91 |
| 20 | 0.321 | 0.029 | 624.75 | 68.3 |
| 21* | 0.214 | 0.043 | 627.73 | 73.93 |

*Denotes Comparative Example.

As shown in Table 6, above, the initial quantum yield performance of the inventive formulations is significantly higher than in the comparative formulations, especially in the case of cadmium free InP dots (InP/ZnS core-shell). The inventive formulations also exhibited less red shift in Example 20 than Comparative Example 21.

The invention claimed is:

1. A method for making polymerizable monomer compositions comprising:

Purifying a (b) monomer mixture of (i) one or more monomers having at least two polymerizable vinyl groups as part of a (meth)acrylate ester group or attached directly to an aromatic ring or a cycloaliphatic group and (ii) one or more monomers having a single polymerizable vinyl group as part of a (meth)acrylate ester group in which the ester contains a cycloaliphatic group or a $C_6$ to $C_{24}$ alkyl group by any one or more of treating the monomer mixture in an activated porous alumina or silica column having, for example, a surface area of from 100 to 300 $m^2/g$; sieve drying the monomer mixture in a vacuum followed by drying over dried molecular sieves having average pore sizes of from 2 to 20 Angstroms; freeze-pump-thaw (FPT) treating by freezing the monomer mixture in a vessel or container to a temperature below −75° C., degassing the monomer mixture by application of vacuum in the range of $10^2$ to $10^{-2}$ Pa), sealing the vessel or container under vacuum, and thawing the composition to room temperature storing the purified monomer mixture (b) in a dry and inert gas; and, combining in an inert atmosphere the resulting monomer mixture (b) with a composition (a) of quantum dots in dry form or in organic solvent solution to make a polymerizable monomer composition that comprises 150 ppm or less of $H_2O$, 100 ppm or less of total polymerization inhibitor compounds and 150 ppm or less of organic radically active molecules.

2. The method as claimed in claim 1 in which the purifying of the monomer mixture (b) comprises freeze-pump-thaw (FPT) treating, followed by drying the resulting treated monomer mixture over a dried molecular sieve.

3. The method as claimed in claim 1 in which the purifying of the monomer mixture (b) comprises degassing the monomer mixture under a vacuum of from $10^2$ to $10^{-2}$ Pa and then treating it in an activated alumina column packed into a disposable polypropylene column.

4. The method as claimed in claim 1 in which the purifying of the monomer mixture (b) comprises degassing the monomer mixture under vacuum of from $10^2$ to $10^{-2}$ Pa and then drying it by exposure to or by mixing with molecular sieves which have been dehydrated at a temperature of from 75 to 200° C. for a period of 4 to 24 hours and kept in an inert atmosphere.

5. The method as claimed in claim 1 in which in the combining of the monomer mixture (b) and the composition (a) of quantum dots, the (a) quantum dots are dried under vacuum to remove any organic solvent before the combining or the polymerizable monomer composition together with the (a) quantum dots is dried under vacuum to remove any organic solvent.

6. The method as claimed in claim 1 in which in the combining of the monomer mixture (b) and the composition (a) of quantum dots, the quantum dots comprise cadmium-free quantum dots.

7. The method as claimed in claim 6 in which the composition (a) of quantum dots comprises core shell cadmium-free quantum dots that have a core shell structure wherein the shell material has a wider band gap than and a small lattice mismatch to the core material.

8. The method as claimed in claim 1 in which the monomer mixture (b) comprises (i) divinyl benzene, tricyclodecane dimethanol diacrylate, isobornyl dimethacrylate, or mixtures thereof and (b)(ii) one or more monomers having a single polymerizable vinyl group as part of a (meth)acrylate ester group in which the ester contains a cycloaliphatic group or a $C_6$ to $C_{24}$ alkyl group.

9. The method as claimed in claim 1 in which the monomer mixture (b) comprises (i) one or more monomers having at least two polymerizable vinyl groups as part of a (meth)acrylate ester group or attached directly to an aromatic ring or a cycloaliphatic group and (b)(ii) isobornyl acrylate (IBOA).

10. The method as claimed in claim 1 wherein the polymerizable monomer composition comprises 150 ppm or less of $H_2O$ as determined by Karl Fisher Titration, and comprises 75 ppm or less of total dissolved oxygen as determined by a photochemical method as described in the reference (J. Polym. Sci. A: Polym. Chem. 2004, volume 42, pages 1285-1292).

* * * * *